United States Patent [19]

Skatteböl et al.

[11] Patent Number: 4,578,484

[45] Date of Patent: Mar. 25, 1986

[54] PROCESS FOR THE PREPARATION OF LINEATIN

[75] Inventors: Lars Skatteböl; Yngve Stenström, both of Oslo, Norway

[73] Assignee: Borregaard Industries Limited, Norway

[21] Appl. No.: 674,629

[22] PCT Filed: Feb. 27, 1984

[86] PCT No.: PCT/NO84/00013

§ 371 Date: Nov. 15, 1984

§ 102(e) Date: Nov. 15, 1984

[87] PCT Pub. No.: WO84/03703

PCT Pub. Date: Sep. 27, 1984

[30] Foreign Application Priority Data

Mar. 15, 1983 [NO] Norway .................................. 830902

[51] Int. Cl.$^4$ ................... C07D 319/04; C07D 323/04
[52] U.S. Cl. ..................................................... 549/360
[58] Field of Search .......................................... 549/360

[56] References Cited

U.S. PATENT DOCUMENTS 4,296,036 10/1981 Mori et al. ........................ 549/360

FOREIGN PATENT DOCUMENTS 0139382 10/1980 Japan ................................. 549/360

*Primary Examiner*—Ethel G. Love
*Attorney, Agent, or Firm*—Wenderoth, Lind & Ponack

[57] ABSTRACT

New process for preparing the pheromone active compound lineatin (3,3,7-trimethyl-2,9-dioxatricyclo[3,3,1,0$^{4,7}$]-nonane), by reacting a 2,2-dimethyl-3,4-pentadienal of formula 1, in which $R_1$ and $R_2$ is each hydrogen or lower alkyl, with β-methylallyl magnesium halide; the formed 2,5,5-trimethylocta-1,6,7-trien-4-ol derivative of formula 2 is subjected to oxidation which does not attack the double bonds; the formed 2,5,5-trimethylocta-1,6,7-trien-4-one derivative of formula 3 is subjected to pyrolysis; the formed 1,4,4-trimethyl-6-methylenebicyclo[3,2,0]heptan-3-one derivative of formula 4 is subjected to oxidation; the resulting 5,5,9-trimethyl-2,6-dioxa-7-oxo-bicyclo[4,2,0]octyl-spiro[2,7]-decane derivative of formula 5 is subjected to oxidation; the resulting 1,5,5-trimethyl-4-oxabicyclo[4,2,0]octan-3,7-dione of formula 6 is reduced in a per se known manner to lineatin of formula 7. Compounds 2, 3, 4 and 5 are novel.

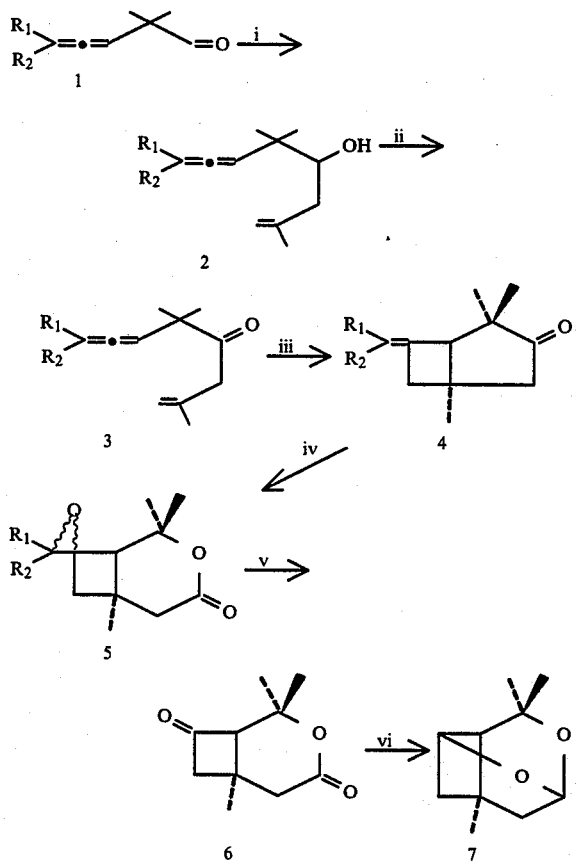

4 Claims, No Drawings

PROCESS FOR THE PREPARATION OF LINEATIN

It is known that lineatin is a pheromone which attracts certain species of ambrosia beetles (Trypodendron). This attraction is particularly strong when lineatin is used in admixture with certain other chemical substances, for instance as described in our Norwegian Pat. No. 144.029.

There are described several processes for the preparation of lineatin, and the following may be mentioned:
A. Borden, J. H.; Handley, J. R.; Johnston, B. D.; MacConnell, J. G.; Silverstein, R. M.; Slessor, K. N.; Swigar, A. A. and Wong, D. T. W. J. Chem. Ecol. 5 (1979) 681.
B. Mori, K. and Sasaki, M. Tetrahedron Lett. (1979) 1329
C. Idem. Tetrahedron 36 (1980) 2197.
D. Slessor, K. N.; Oehlschlager, A. C.; Johnston, B. D.; Pierce, H. D. Jr.; Grewal, S. K. and Wickremesinghe, L. K. G. J. Org. Chem. 45 (1980) 2290
E. McKay, W.; Ounsworth, J.; Sum, P.-E. and Weller, L, Can. J. Chem. 60 (1982) 872.
F. Mori, K.; Uematsu, T.; Minobe, M. and Yanagi, K. Tetrahedron Lett. 23 (1982) 1921.
G. White, J. D.; Avery, M. A. and Carter, J. P. J. Am. Chem. Soc. 104 (1982) 5486.

None of these known processes can be considered as satisfactory with respect to yield, economy and simple operation. Thus, several are carried out by using photochemical reactions, which may easily give rise to considerable problems, particularly when carried out in large scale.

According to the invention there has been found a new process which leads to the desired lineatin with satisfactory yield by using commercially available cheap reagents and solvents, without using photochemical reactions.

The process according to the invention may be illustrated as follows:

$R_1$ and $R_2$ may be hydrogen or lower alkyl. The examples illustrate $R_1=R_2=H$ (a) and $R_1=R_2=CH_3$ (b).

The preparation of 1 may be carried out in a per se known manner (U.S. Pat. No. 3,236,869) by reacting isobutyraldehyde with propargylalcohol ($R_1=R_2=H$) or a suitable derivative thereof in the presence of a catalyst such as p-toluene sulfonic acid.

STEP i

The preparation of the new compound 2 suitably takes place in a per se known manner (Bly et al, J. Am. Chem. Soc. 91 (1969) 3292) by reacting 1 with a suitable Grignard reagent, such as $\beta$-methyl allylmagnesium chloride.

STEP ii

The preparation of the new compound 3 also takes place in a per se known manner [Brown et al, J. Am. Chem. Soc. 83 (1961) 2952 and J. Org. Chem., 36 (1971) 387] by oxidizing 2 with a mild oxidizing agent which oxidizes the secondary hydroxyl group to a keto group without attacking the double bond in 2. Suitable oxidizing agents are for instance bichromate, Jones reagent and DMSO.

STEP iii

The preparation of the new compound 4 from 3 is an important feature of the invention.

Here the reaction is a thermal intramolecular cycloaddition in which the reaction conditions are dependant upon several factors, including the groups $R_1$ and $R_2$. In order to attain complete reaction it is necessary that the compound 3 is kept for some time at a specific temperature. In practice the reaction may be carried out by distilling the compound through a suitably heated tube under reduced pressure. Too high temperatures, such as above 550° C., may result in excessive amounts of other products such as 8 due to competing reactions, while too low temperatures, such as below 400° C., will result in incomplete reaction. The lower the reaction temperature is, the longer the reaction time must be. The reac-

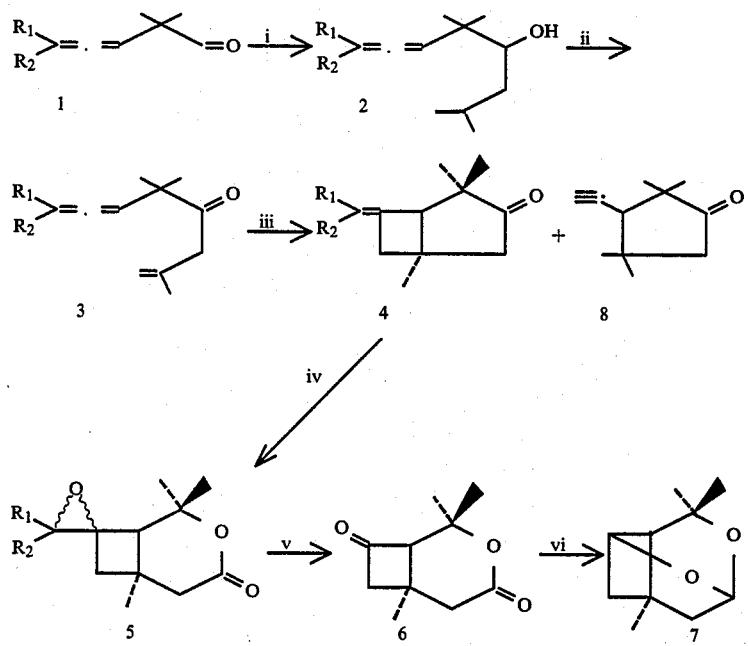

tion time may for instance be adjusted by varying the pressure when the compound 3 is distilled through a heated tube, since higher pressure will result in a longer residence time in the reactor. Normally the pressure is kept lower than 10 mm Hg. It is also possible to extend the residence time (reaction time) by using a longer reactor and/or increase the resistance therein. When for instance $R_1=R_2=H$ and the length and the diameter of the tube are 60 cm and 2.5 cm respectively, and it is packed with silica wool, the suitable temperature will be 470°–510° C., preferably 480°–500° C., in particular about 490° C.

STEP iv

Compound 4 is converted to the new compound 5 by simultaneous ring expansion of the cyclopentane ring and oxidation of the double bond by means of a suitable oxidizing agent, particularly an organic peracid such as an optionally substituted perbenzoic acid or pertrifluoro acetic acid.

STEP v

Compound 5 is converted to compound 6 by further oxidation. A suitable oxidizing agent is periodic acid or a periodate in acidic medium.

STEP vi

The conversion of compound 6 to lineatin 7 takes place in a known manner by reduction, for instance as described in E above with diisobutyl aluminium hydride.

Among the previously suggested syntheses of lineatin only six may be compared with the present process, since Borden et al (A) does not give any yield or experimental details for the synthesis.

In the following a comparison has been made between the syntheses by considering (a) number of steps, (b) percent total yield from commercially available starting materials and (c) photochemical step. The latter has been included since it may present great problems to carry out photochemical reactions in a larger scale as mentioned above. They also require special equipment.

| Synthesis | Number of steps | Total yield % | Photochemistry |
|---|---|---|---|
| B | 9 | 0.14 | yes |
| C | 8 | 0.26 | " |
| D | 9 | 2 | no |
| E | 9 | 6 | yes |
| F | 9 | 3 | no |
| G | 11 | 8 | yes |
| Invention | 7 | 11 | no |

The present process is clearly superior according to this comparison. There are of course other factors which are essential, such as the price of reagents and solvents used, methods of separation and difficulty in carrying out the operations. The present process is in these respects most favourable. It is based on generally cheap reagents and ordinary solvents. The separation generally takes place by distillation. The total yield according to the present process is based on propargyl alcohol and isobutyraldehyde, which are both cheap chemicals.

Examples of the individual process steps are given below.

Unless otherwise is mentioned, the NMR spectra have been recorded on a Varian 60 MHz instrument.

EXAMPLE 1

2,2-dimethyl-3,4-pentadienal (1a) was prepared according to U.S. Pat. No. 3,236,869 from propargyl alcohol and isobutyraldehyde in tetraline or 1,3-diisopropylbenzene with p-toluene sulphonic acid as catalyst. Yield 34–39%. The product 1a was characterized by GC, NMR and IR. Bp. 131° C. (lit. 131° C.).

EXAMPLE 2

2,2,5-trimethyl-3,4-hexadienal (1b) was prepared according to Bly et al (see above) from 2-methyl-3-butyn-2-ol, isobutyraldehyde, benzene and catalytic amounts of p-toluene sulphonic acid. Distillation gave a yield of 50% (lit. 38%). The product 1b was characterized by GC (>98% pure), NMR and IR. Bp. 103° C./100 mm Hg (lit. 96°–9° C./104 mm Hg).

EXAMPLE 3

2,5,5-trimethylocta-1,6,7-trien-4-ol (2a). 300 ml of absolute ether were added to 7.29 g (0.30 mole) of dry Mg, the mixture was cooled to 15±1° C., and 27.19 g (0.30 mole) freshly distilled β-methylallyl chloride were added. The mixture was stirred over night at the same temperature. The white suspension was cooled to 0° C., and 11.03 g (0.10 mole) 1a in 150 ml absolute ether were added dropwise during 1 hour. The mixture was stirred at 0° C. for 4 hours (reaction monitored on GC). 37 ml of saturated NH4Cl solution were added with vigorous stirring. The solution was decanted from the magnesium salts which were washed several times with ether. The combined ether phases were dried (MgSO4). Distillation gave 14.22 g (91%) 2a, b.p. 60°–1° C./1.5 mm Hg.

IR (film): 3580 (m), 3490 (m), 3085 (m), 2980 (s), 2945 (s), 2885 (m), 1960 (s), 1653 (m), 1465 (m), 1395 (m), 1382 (m), 1300 (m), 1270 (m), 1180 (m), 1068 (s), 997 (m), 893 (s), 847 (s), 645 (w) cm$^{-1}$.

$^1$H NMR (CCl4): δ 1.02 (s, 6H), 1.53 (bs, 1H), 1.73 (bs, 3H), 1.88–2.22 (m, 2H), 3.30 (dd, J$_1$ 3 Hz, J$_2$ 10 Hz, 1H), 4.56–5.23 (m, 5H).

EXAMPLE 4

2,5,5,8-tetramethylnona-1,6,7-trien-4-ol (2b) was prepared as described for 2a from 8.72 g (0.36 mole) of Mg, 32.65 g (0.36 mole) of β-methylallyl chloride and 16.61 g (0.12 mole) of 1b. The work up resulted in 21.44 g (92%) of 2b. Bp. 61°–2° C./0.3 mm Hg, n$_D^{16}$ 1.4810.

IR (film): 3474 (s), 3070 (m), 2960 (s), 2860 (s), 2705 (w), 1966 (m), 1642 (m), 1437 (s), 1361 (s), 1287 (m), 1183 (m), 1058 (s), 1010 (m), 884 (s), 806 (m) cm$^{-1}$.

$^1$H NMR (CCl4): δ 0.95 (s, 6H), 1.50–2.43 (m, 11H), 2.98 (bs, 1H), 3.28 (dd, J$_1$ 3 Hz, J$_2$ 10 Hz, 1H), 4.67–5.00 (m, 3H).

EXAMPLE 5

2,5,5-trimethylocta-1,6,7-trien-4-one (3a). Brown's oxidation method (see Brown et al above) was used. The oxidizing reagent was prepared as described in the literature. 35.20 g (0.21 mole) of 2a were dissolved in a 100 ml of ether, and with vigorous stirring the oxidation reagent was added very slowly until the alcohol had reacted according to GC (about 4 days). 355 ml of the reagent (corresponding to 0.234 mole of Na2Cr2O7) had then been added. The organic phase was separated, and the aqueous phase was extracted with ether (3×75 ml). The combined organic phases were extracted with saturated NaHCO3 (1×75 ml) and water (1×50 ml), dried (MgSO₄), evaporated and distilled. The yield was 30.90 g (90%) of 3a.

Jones oxidation was carried out on 2a. A large excess of the oxidizing agent had to be added for complete reaction, which resulted in a more difficult work up than by Brown's method and which also gave a poorer yield (78%).

3a, b.p. 63°–5° C./3.5 mm Hg. IR (film): 3085 (m), 2980 (s), 2940 (s), 1957 (s), 1715 (s), 1653 (m), 1467 (m), 1391 (m), 1370 (m), 1325 (m), 1225 (w), 1153 (w), 1060 (m), 1035 (m), 1003 (w), 892 (s), 847 (s), 787 (w) cm$^{-1}$.

$^1$H NMR (CDCl₃): δ 1.23 (s, 6H), 1.72 (bs, 3H), 3.23 (s, 2H), 4.63–5.33 (m, 5H).

The 2,4-dinitrophenylhydrazone of 3a (recrystallized from ethanol), m.p. 63°–4° C.

EXAMPLE 6

2,5,5,8-tetramethylnona-1,6,7-trien-4-one (3b), was prepared as described for 3a from 10.00 g (51.5 mmole) of 2b. Work up as above gave 8.9 g (90%) of 3b, bp. 70°–2° C./0.5 mmHg, $n_D^{16}$ 1.4754.

IR (film): 3073 (m), 2966 (s), 1961 (w), 1778 (w), 1702 (s), 1647 (m), 1442 (s), 1361 (s), 1314 (s), 1239 (m), 1187 (m), 1055 (s), 1011 (m), 967 (w), 942 (s), 885 (s), 837 (w), 801 (m) cm$^{-1}$.

$^1$H NMR (CCl₄) δ 1.17 (s, 6H), 1.70 (s, 6H), 1.73 (s, 3H), 3.14 (s, 2H), 4.57–5.03 (m, 3H).

EXAMPLE 7

1,4,4-trimethyl-6-methylenebicyclo[3.2.0]heptan-3-one (4a). 5.00 g (32.4 mmole) of 3a were distilled through a 60 cm long quartz tube packed with 14 g of silica wool and heated to 490±5° C. at 0.5 mm Hg. The reaction was monitored by allene absorption on IR. After distillation twice all the allene had reacted. Two products 4a and 8 of 60 and 20% percent respectively, dominated the mixture which was distilled through a good column (Fischer Spaltrohr, 60 theoretical bottoms). 41.4 g of a 5% (w/w) ethanolic (96%) AgNO₃ solution were added to the distillate, and after some hours 8 had been precipitated as the silver acetylide (9) (not shown). It was filtered off and air dried. The filtrate was concentrated by distillation at atmospheric pressure. Distillation gave 2.31 g (46%) of 4a, bp. 69°–70° C. (4 mm Hg), mp. −23° to −20° C.

Analysis: Calculated for C₁₁H₁₆O: C 80.44, H 9.82 Found: C 79.69, H 9.60%.

4a: IR (film): 3085 (w), 2970 (s), 2875 (m), 1743 (s), 1718 (m), 1675 (m), 1460 (m), 1382 (m), 1095 (m), 882 (m) cm$^{-1}$.

$^1$H NMR (CDCl₃, 400 mHz), δ 1.08 (s, 3H), 1.09 (s, 3H), 1.43 (s, 3H), 2.28 (d, J 18 Hz, 1H), 2.37 (dq, J₁ 14 Hz, J₂ 2.8 Hz, 1H), 2.57 (2s, J₁ 18 Hz, J₂ 14 Hz, 2H), 2.79 (q, J 2.8 Hz, 1H), 4.88 (q, J₁ 2.8 Hz, J₂ 4 Hz, 1H), 4.92 (q, J₁ 2.8 Hz, J₂ 4 Hz, 1H).

$^{13}$C NMR (CDCl₃, 50.3 MHz): δ 19.1 (CH₃), 27.1 (CH₃), 27.9 (CH₃), 34.4

(cyclobutane—C—), 43.4 (cyclobutane—CH₂—), 49.3 (cyclopentane—CH₂—), 50.2 (cyclopentane—C—), 61.6 (—C—H), 111.5 (CH₂=), 144.7 (>C=), 221.8 (>C=O).

Mp. for the 2,4-dinitrophenylhydrazone of 4a: 119°–120° C.

2.68 g (6.1 mmoles) of 9 were added to 0.75 g (15.3 mmoles) of NaCN in 5 ml of water, refluxed for 4 hours until all had been dissolved, cooled, extracted with ether, dried (MgSO₄) and evaporated. This gave 0.92 g of pure 8 while at the same time the silver was recovered.

—8: M.p. 61°–62° C., Bp. 69°–70° C./4 mm Hg.

IR (CDCl₃): 3315 (s), 2970 (s), 2940 (m), 2885 (m), 2125 (w), 1743 (s), 1468 (m), 1412 (w), 1385 (m), 1375 (m), 1235 (m) cm$^{-1}$.

$^1$H NMR (CDCl₃): 1.13 (s, 3H), 1.15 (s, 3H), 1.20 (s, 3H), 1.25 (s, 3H), 2.25 (s, 2H), 2.27 (d, J 3 Hz, 1H), 2.68 (d, J 3 Hz, 1H).

$^{13}$C NMR (CDCl₃, 50.3 MHz) δ 22.8 (CH₃), 24.4 (CH₃), 27.5 (CH₃), 29.5 (CH₃), 37.1 (C-4, >C<), 47.9 (C-2, >C<), 51.6 (CH) and 52.1 (CH₂), 74.0 (≡C—H), 80.6 (—C≡), 221.2 (C=O).

EXAMPLE 8

6-isopropylidene-1,4,4-trimethylbicyclo[3.2.0]heptan-3-one (4b). 5.00 g (26.0 mmoles) of 3b were distilled through the same column as used for 3a. The reaction was monitored on GC. The main product 4b was separated by distillation on a good column (Fischer Spalt rohr, 60 theoretical plates) with >97% purity. The yield was 2.55 g (51%). Bp. 68° C./0.2 mm Hg.

IR (film): 2920 (s), 2861 (s), 2824 (m), 2721 (w), 1735 (s), 1449 (s), 1409 (m), 1376 (s), 1359 (m), 1303 (m), 1286 (m), 2141 (m), 1206 (m), 1158 (w), 1120 (s), 1085 (m), 1055 (m), 1042 (m), 911 (m), 898 (m), 868 (w), 707 (w) cm$^{-1}$.

$^1$H NMR (CDCl₃): 1.00 (s, 3H), 1.10 (s, 3H), 1.37 (s, 3H), 1.50 (bs, 6H), 2.28 (bs, 3H), 2.40 (b s, 1H), 2.73 (b s, 1H).

EXAMPLE 9

5,5,9-trimethyl-2,6-dioxa-7-oxobicyclo[4.2.0]octylspiro[2,7]-decane (5a). 2.96 g (18.0 mmoles) of 4a were dissolved in 40 ml of dry CH₂Cl₂. 8.05 g 81% (corresponding to 6.52 g and 37.8 mmoles) of m-chloroperbenzoic acid (m-CPBA) and 3.86 g (46.0 mmoles) of NaHCO₃ were mixed and added to the above solution. The mixture was stirred over night at room temperature, and 35 ml of 10% Na₂S₂O₃ were then added. After half an hour's stirring, the organic phase was separated, and the aqueous phase was extracted with CH₂Cl₂ (2×20 ml). The combined organic phases were washed with a saturated NaHCO₃ solution (1×20 ml) and saturated NaCl solution (1×20 ml), dried (MgSO₄) and evaporated. The crude product weighed 3.58 g (100%) and was pure according to GC. It was used for the next reaction without further purification.

5a: $^1$H NMR (CDCl₃, 98 MHz): δ 1.27 (s, 3H), 1.40 (s, 3H), 1.45 (s, 3H), 2.15 (d, J 13 Hz, 1H), 2.36 (d, J 13 Hz, 1H), 2.56–2.81 (m, 4H), 3.42 (d, J 4 Hz, 1H).

MS (CI, isobutane) m/z 197 (M+ + 1).

EXAMPLE 10

3,3,5,5,9-pentamethyl 2,6-dioxa-7-oxobicyclo[4.2.0]octylspiro[2.7]decane (5b) was prepared in the same manner as described for 5a from 0.5 g (2.60 mmoles) of 4b, 1.16 g of 81% (corresponding to 0.94 g and 5.46 mmoles) m-CPBA and 0.54 g (6.37 mmoles) of NaHCO₃. Work up as above gave 0.59 g (100%) of the crude product which was pure (GC) and was used directly further.

EXAMPLE 11

1,5,5-trimethyl-4-oxabicyclo[4.2.0]octan-3,6-dione (6)

(i) From 5a. To a solution of 3.53 g (18 mmoles) 5a in 30 ml of absolute ether, 4.10 g (18 mmoles) of $H_5IO_6$ were added with vigorous stirring. The mixture was stirred over night, and 5 ml of water were added. The ether phase was separated, and the aqueous phase was extracted with ether (2×15 ml). The combined ether phases were extracted with saturated $Na_2CO_3$ solution (1×20 ml) and saturated NaCl solution (1×20 ml), dried ($MgSO_4$) and evaporated. The crude product is 3.29 g (100%) of a crystalline compound (mp. 99°–100° C.) which has the same IR, NMR and MS data as given in the literature (C).

(ii) From 5b. To a solution of 0.59 g (2.60 mmoles) crude 5b in 5 ml ether 0.60 g (2.60 mmoles) $H_5IO_6$ were added in the same manner and worked up as above. The product consisted of 6 and two other compounds. Recrystallization from t-butyl methyl ether afforded 0.33 g (70%) of 6.

EXAMPLE 12

(±) lineatin (7). The ketolactone 6 (3.20 g, 17.6 mmoles) was suspended in 70 ml of dry ether and cooled to −60° C. 39 ml of 1.0M (39 mmoles) diisobutylaluminium hydride in hexane were added dropwise with stirring. The temperature of the solution was kept between −70° and −60° C. The solution was stirred at this temperature for about 2 hours. 64 ml of saturated $NH_4Cl$ solution were slowly added dropwise before the solution was heated to 0° C., and it was then acidified with 46 ml of 4N HCl. The solution was further stirred for 1.5 hours. Extraction with ether (4×60 ml), washing of the combined ether phases with a saturated $NaHCO_3$ solution (1×60 ml), drying ($MgSO_4$) and evaporation at moderate vacuum (the temperature in the bath was <35° C.) resulted in a crude product which upon distillation (bp. 60°–62° C./3 mm Hg) gave 2.17 g of 7 (74%). The spectroscopic data were in agreement with those of the literature.

EXAMPLE 13

(±) lineatin (7). $LiAl(OBu^t)_3H$-reduction of 6. To a stirred solution of 3.99 g (21.9 mmoles) 6 in 300 ml abs. ether at room temperature, 11.4 g (44.9 mmoles $LiAl(OBu^t)_3H$ were added portion-wise during ½ h. The suspension was stirred overnight and then 60 ml of 4M aqueous HCl were added. The solution was stirred for further 1.5 h. Extraction with ether (3×60 ml), washing of the combined ether phases with saturated $NaHCO_3$ (1×60 ml), drying ($MgSO_4$), and careful distillation gave 1.90 g (52%) 7, b.p. 60°–2° C./3 mm Hg.

We claim:

1. Process for the preparation of lineatin (3,3,7-trimethyl-2,9-dioxatricyclo[3,3,1,0^{4,7}]nonane) of the formula

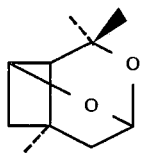

characterized in that (i) a 2,2-dimethyl-3,4-pentadienal of the formula

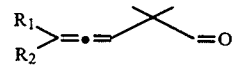

in which $R_1$ and $R_2$ each is hydrogen or lower alkyl, is reacted with β-methylallyl magnesiumhalide, (ii) the formed 2,5,5-trimethylocta-1,6,7-trien-4-ol derivative of the formula

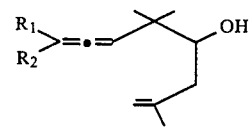

is subjected to oxidation which does not attack the double bonds, (iii) the formed 2,5,5-trimethylocta-1,6,7-trien-4-one derivative of the formula

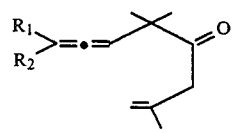

is subjected to pyrolysis, (iv) the formed 1,4,4-trimethyl-6-methylene-bicyclo[3,2,0]-heptan-3-one derivative of the formula

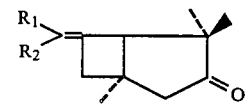

is subjected to oxidation with an organic peracid, (v) the resulting 5,5,9-trimethyl-2,6-dioxa-7-oxobicyclo[4,2,0]octylspiro[2,7]decane derivative of the formula

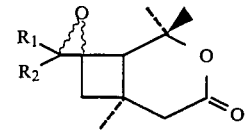

is subjected to oxidation with a periodate in acidic medium, (vi) the resulting 1,5,5-trimethyl-4-oxabicyclo[4,2,0]-octan-3,7-dione of the formula

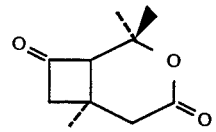

is reduced to lineatin.

2. Process according to claim 1, characterized by using a starting material in which $R_1$ and $R_2$ are the same and are hydrogen or methyl.

3. Process according to claim 1, characterized in that the oxidation in step (ii) is carried out with chromate or dichromate in acidic medium.

4. Process according to claim 1, characterized in that the pyrolysis in step (iii) is carried out at 470°–510° C., preferably 480°–500° C.

* * * * *